United States Patent [19]

Steck

[11] 4,282,253

[45] Aug. 4, 1981

[54] TOPICAL PROPHYLAXIS AGAINST SCHISTOSOMIASIS

[75] Inventor: Edgar A. Steck, Silver Spring, Md.

[73] Assignee: The United States of America as represented by the Secretary of the Army, Washington, D.C.

[21] Appl. No.: 94,259

[22] Filed: Nov. 14, 1979

[51] Int. Cl.³ .......................................... A61K 31/135
[52] U.S. Cl. .................................................... 424/330
[58] Field of Search ........................................ 424/330

[56] References Cited

PUBLICATIONS

Muftic–Chem. Abst. vol. 74 (1971), p. 15721n.
Pellegrino–Experimental Parasitology, vol. 21 (1967), pp. 112–131.
Austin et al., Amer. J. Trop. Med. Hyg., vol. 22 (1973), pp. 743–747.
Gilbert et al., J. Parasitology, vol. 56 (1970), pp. 397–398.
Hunter et al., Amer. J. Trop. Med. Hyg. vol. 5 (1956) pp. 713–736.
Nolan et al., Amer. J. Trop. Med. Hyg., vol. 4 (1955), pp. 152–155.
Mueller–Chem. Abst. vol. 64 (1966), p. 4844g.
Gottstein et al., J. Org. Chem., vol. 30 (1965), pp. 2072–2073.

*Primary Examiner*—Sam Rosen
*Attorney, Agent, or Firm*—William G. Gapcynski; John M. Petruncio

[57] ABSTRACT

An improved method is provided for the prevention of schistosomiasis in higher animals. The topical application of a composition containing a dehydroabietylamine or a derivative thereof provides a coating of perdurable anti-penetrant through which the infective cercariae of the parasitic worm do not pass readily.

16 Claims, No Drawings

TOPICAL PROPHYLAXIS AGAINST SCHISTOSOMIASIS

BACKGROUND OF THE INVENTION

Schistosomiasis (also known as bilharziasis, after Theodor Bilharz who identified the parasites) is a state of infection with leaf-like flat worms belonging to one or more species of blood flukes known as Schistosomatidae. Schistosomiasis is the most important among diseases caused by worms. Some 200 million people are infected by blood flukes (trematodes) in regions of Europe, Asia, South America, and also the Caribbean area. The disease complex results from infection by three major species of digenetic trematodes, viz., Schistosoma mansoni, S. japonicum, and S. haematobium. Fundamentally, an infected fresh water snail sheds free swimming infective forms (cercariae) into the water, and man (or other animal) is infected by the penetration of the parasite through the skin, followed by maturation of the worms (male and female) in the body, pairing of male and female worms, shedding of eggs in excrement into water where development occurs and host snails are then invaded for continuation of the cycle. In the mammalian host, the schistosomes enter blood circulation and pass through the lungs to mature in the liver, then reside in mesenteric-portal or pelvic veins. Eggs are shed by the female into the lumen of the small intestine in the case of S. japonicum, the bladder (S. haematobium, or, rarely S. mansoni). Most of the pathological effects resulting from schistosome infections derive from the spined eggs, both within the body and in being shed in the urinary or fecal stream. Specific primary clinical problems occur in the intestine and bladder, together with secondary ones in liver, spleen, and lungs, plus variable involvement of the central nervous system and retina. The worms live for years (immune response of the host has little effort on established adult schistosomes, but does work against development of new infections. Pathological changes in schistosomiasis are considerably variable with the species and strain of parasite, duration of the infection, intercurrent infections, and nutritional state of the host.

Treatment of the schistosomiases does not reverse the damage already done the host by the parasitic worms. Anti-schistosomal agents generally impair the production of eggs and hinder development and functions of the flukes, with or without actually killing them. "Cure" is said to be achieved when viable eggs are no longer found in the excrement. Such criterion does not imply absence of worms, it must be understood. Successful treatment of the schistosomiases is difficult to achieve safely, for anti-schistosomal agents are appreciably toxic to the host. Suppressive management of schistosomiasis through administration of drugs at regular intervals may also be hazardous to the patient. Treatment of the infections is increasingly difficult in the sequence: S. haematobium, S. mansoni, and S. japonicum. That is essentially the same as the general extent of severity of the consequences of those schistosomiases.

Control of schistosomiasis through interruption of the life cycle of the parasite is a more attractive course of action than treatment of the infection. Two points at which control may be exercised include eradication of the snail intermediate host and prevention by protection of the mammalian final host against the cercariae shed by the snails. Various means have been tried to eliminate snails, for example, molluscicides and biological control; however, the basic problems have not been solved and even 0.2% of a snail population being infected renders a region highly endemic to schistosomiasis. Prevention of schistosomiasis, in sensu stricto, involves protection of man or other final host against infection by cercariae of the trematodes. In this regard, it would be desirable to have perdurable topical agents which, when applied to the skin, could afford means of safely preventing schistosomiasis. Hitherto, this goal has not been achieved.

It is known that various agents, when applied topically, provide some extent of protection of a final host against infection by penetration of the cercariae of Schistosoma mansoni or S. japoniucm. On the practical assessment of the results, however, the protective effects decrease markedly if the surface is exposed to washing or exposed to running water. Therefore, such topical agents offer little advantage in use by personnel (civilian or military) who may be exposed to waters containing schistosome-bearing snails. Practical utility of a topical anti-penetrant must include: resistance to washing action of flowing water, lack of irritant characteristics to the skin, ease of application, and low cost.

SUMMARY OF THE INVENTION

Accordingly, it is an object of this invention to provide perdurable topical agents useful in the prevention of schistosomiasis.

It is another object of the invention to provide topical agents which are resistant to the washing action of flowing water.

It is another object of the invention to provide topical agents which are non-irritating when applied to the skin.

It is another object of the invention to provide topical agents which are inexpensive and easy to apply.

Yet other objects of the invention will become apparent to one of ordinary skill upon reading this disclosure.

The above objects are achieved by the method of this invention for preventing schistosomiasis in a mammal which comprises: applying to the skin of said mammal a composition which contains dehydroabietylamine or a derivative thereof in order to achieve an antipenetrant effect against cercariae of infectious schistosome parasites. Preferred agents are dehydroabietylamine, its salts, and its ethylene oxide adducts.

The present invention relates to novel means for protecting mammalian species against infection by schistosome species. It is based upon preventing access of cercarial forms of the worms through the skin by topical application of compositions containing perdurable anti-penetrant agents. Broadly, the anti-penetrant agents are dehydroabietylamine and its derivatives, which protect mammals against infective cercariae of the parasitic worm. Preferred agents are dehydroabietylamine, its salts, and its ethylene oxide adducts. These novel anti-penetrants are perdurable and more resistant to removal by washing than other compositions. Evidence indicates that they are effective in barring entry of the cercariae of the various Schistosoma species, including S. japonicum, which is well known for producing infections upon exposure to only a few cercariae.

The anti-penetrant agents used in the method of this invention offer safe, easy, and cheap means for protection of civilian populations and troops against infection by schistosomiasis, as will be apparent from the detailed description below.

DETAILED DESCRIPTION OF THE INVENTION

The compositions of the invention may be applied to the skin by any suitable means in protecting against penetration by cercariae of schistosome worms. Exemplary vehicles for achieving uniform application include: solutions (as, an alcoholic menstrum); creams (as, vanishing cream); ointment (as, white or yellow ointment); liniment (as, green soap tincture); or malagma (as, an emollient oil). The anti-penetrant may remain on the skin for hours without decrease in effectiveness and without irritation, and exposure to water will not readily remove the agent. Accordingly, persons who are protected by the method of this invention may be exposed to schistosome-infected waters, whether for civilian or military purposes, with minimal hazards of skin penetration by cercariae of the worms.

The concentration of anti-penetrant agent in the composition is not critical, and one of ordinary skill may readily determine a suitable concentration. In general, of course, lower concentrations have an advantage from the standpoint of economics and lack of irritation. A preferred range of concentration of anti-penetrant agent in the composition is from about 1% to about 20% weight/volume (w/v). A more preferred range is from about 1% to about 10% w/v, and an even more preferred range is from about 1.25% to about 5% w/v.

When salts of dehydroabietyamine are employed, again, the particular salt selected is not critical. One of ordinary skill will routinely select an appropriate salt, for example, a pharmaceutically-acceptable acid addition salt. Salts derived from organic or inorganic acids may be used, non-limiting examples being the acetate, sulfate, benzoate, napthaleneacetate, and hydrochloride salts. Preferred among the salts is the acetate salt.

The following non-limiting examples are now provided, merely to illustrate the invention:

MATERIALS

For practical reasons, only commercial grade materials were used in the work on prophylaxis of schistosomiasis. Variability from lot-to-lot appeared to be of little consequence in performance in the tests.

The technical grade dehydroabietylamine was ordinarily a viscous liquid designated Amine $D^R$ or Amine $750^R$ by Hercules, Inc.; however, other dehydroabietylamine samples of at least 90% amine content were also used. Compositions of the acetate salt of dehydroabietylamine were of 50% or 70% solids content derived from the technical grade amines. Ethylene oxide adducts of technical grade dehydroabietylamine were also employed as anti-penetration agents. The products contained 5 moles of ethylene oxide in an adduct with 15% of free amine (Polyrad $0515^R$), 11 moles of ethylene oxide in the adduct with either no free amine (Polyrad $1100^R$) or 10% of free amine (Polyrad $1110^R$).

METHODS

(a) Drug Preparation

Preferred vehicles used for dissolving the drugs included methanol or ethanol, and the highest concentration of drugs was usually 5% w/v.

(b) Prophylactic Trials: S. mansoni

The experimental animals were female ICR/FG mice, 9-10 weeks old (28-33 g.) which were held for 1 week prior to use. In the initial trials of drugs, 5 mice were used per dose level of drugs, together with appropriate controls. The mice were placed in a special restrainer and tails were wiped clean and dry with isopropyl alcohol before the tails were immersed in the drug solution for 5 minutes. During immersion of the tails, complete coverage with drug solution was ensured by washing with the solution while in the restrainer, and the tails were dried in a current of air during 1-2 hours. Following drug exposure, the mice were retained for 24 hours without or with washing of the tails in flowing warm tap water for 30 minutes.

At the end of the pre-exposure handling, each mouse was placed in a restrainer and the tail exposed to S. mansoni parasites (100 cercariae per mouse) for 45-90 minutes. Following exposure, the mice were kept in plastic boxes lined with heat-sterilized sawdust until the tails were dry, then transferred to stainless steel cases, 5 per cage. The animals were observed daily for 7 weeks, until killed with sodium pentobarbital-heparin. Evidence of drug toxicity was indicated in deaths occurring 12-24 hours after treatment. Survivors at ($49 \pm 3$) days were killed and the livers perfused to determine the total burden of adult worms, following the method of Radke et al, J. Parasitol. 47: 366-68 (1961).

(c) Prophylactic Trials: S. japonicum

Because of the characteristics of S. japonicum cercariae, it was not satisfactory to expose mice to cercarial-infected water, either by immersing the tail or by pipetting parasites onto the shaven belly.

Mice were anesthetized (cf. D. G. Erickson, J. Parasitol. 60: 553-54 (1974) and the bellies trimmed and shaven. A loop of 5 or 6 mm. diameter made from suture material, attached to an applicator, was used to transfer 20 to 30 cercariae of S. japonicum (counted individually) to the bellies of the mice. There was penetration within 5 minutes for controls (five to a group minimum). In testing of drugs, the alcoholic solutions were painted on the bellies 24 and 48 hours prior to exposure of the mice to cercariae of S. japonicum. Otherwise, the trials were done as with S. mansoni, using a 7 week holding period.

RESULTS

EXAMPLE 1. DEHYDROABIETYLAMINE

Technical dehydroabietylamine of 92-94% amine content was dissolved in ethanol to give 5% w/v solution and diluted to obtain 2.5% and 1.25% solutions.

In the anti-penetration test on the shaved bellies of mice, 99 to 100% protection was afforded against penetration by S. japonicum cercariae through prior application of the amine solutions of 2.5% and 5% concentration. No evidence of irritation resulted from dehydroabietylamine to the shaved skin of mice.

The prior application of dehydroabietylamine in ethanol to tails of mice gave excellent protection against infection by S. mansoni. A tabulation (Table 1) shows the results of multiple trials in which no penetration by cercariae occurred among treated mice.

EXAMPLE 2. DEHYDROABIETYLAMINE ACETATE

The acetate salt of dehydroabietylamine was available in the form of technical-grade compositions. One was a tan colored paste containing 70% solids and 30% water. The other was an aqueus alcoholic solution of the salt which held 50% of solids. Each water soluble amine acetate was used as obtained to prepare 5% alcoholic solutions and then diluted with ethanol for 2.5% and 1.25% solutions.

Testing for anti-penetration effects of the amine acetate preparations was done on shaved bellies or backs of mice restrained during application of *S. japonicum* cercariae. Little difference in protection was apparent whether the compound was applied 24 or 48 hours prior to exposure. The extent of protection was 91–100% for 5% solutions of the amine acetate preparations and 49 to 81% for 2.5% solutions.

Tables 2 and 3 show, respectively, the anti-penetrant effects of alcoholic preparations made from the 70% amine acetate paste or the 50% solution of the salt when tested using *S. mansoni* cercariae. Excellent protection was afforded, never falling below 94% of animals exposed.

EXAMPLE 3. ETHYLENE OXIDE ADDUCTS OF DEHYDROABIETYLAMINE

So-called oxyethylated amines were formed from technical dehydroabietylamine by interaction with ethylene oxide. The adducts had the general structure

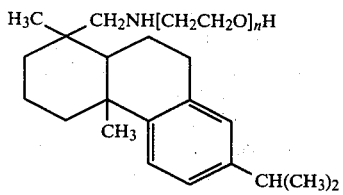

where n was 5 or 11. In the case of n=5, there was present 15% of dehydroabietylamine; where n=11, 10% of dehydroabietylamine was unchanged. Solutions of the material were prepared on the weight/volume basis without considering the composition of the technical-grade product. The stock solution was 5% in methanol.

The amine adducts were screened for protective effects against *S. mansoni* cercariae in the usual way. The data assembled in Table 4 were from use of the adduct with 5 moles of ethylene oxide, and those in Table 5, the adduct with 11 moles of ethylene oxide.

TABLE 1
Dehydroabietylamine: Antipenetrant Effects vs. *S. mansoni* Cercariae in Mice

| Time | Conc. | Surv. | Mean Worm Burden Treated | Mean Worm Burden Control | % of Control |
|---|---|---|---|---|---|
| 24 Hours | 5 | 5/5 | 0 | 33.8 | 0.0 |
| 24 Hours | 2.5 | 5/5 | 0 | 33.8 | 0.0 |
| 48 Hours | 5 | 5/5 | 0 | 33.8 | 0.0 |
| 48 Hours | 2.5 | 5/5 | 0 | 33.8 | 0.0 |
| 24 Hours | 5 | 5/5 | 0 | 14.6 | 0.0 |
| 24 Hours wash | | 5/5 | 0 | 11.0 | 0.0 |
| 24 Hours | 2.5 | 5/5 | 0 | 31.4 | 0.0 |
| 24 Hours wash | | 5/5 | 0 | 30.6 | 0.0 |
| 24 Hours | 1.25 | 5/5 | 0 | 31.4 | 0.0 |
| 24 Hours wash | | 5/5 | 0 | 30.6 | 0.0 |

TABLE 2
Dehydroabietylamine Acetate: Antipenetrant Effects of 70% Preparation vs. *S. mansoni* Cercariae in Mice

| Time | Conc. | Surv. | Mean Worm Burden Treated | Mean Worm Burden Control | % of Control |
|---|---|---|---|---|---|
| 24 Hours | 5 | 5/5 | 0 | 30.0 | 0.0 |
| 24 Hours | 2.5 | 5/5 | 0 | 30.0 | 0.0 |
| 48 Hours | 5 | 5/5 | 0 | 30.0 | 0.0 |
| 48 Hours | 2.5 | 5/5 | 0 | 30.0 | 0.0 |
| 48 Hours | 5 | 5/5 | 0 | 24.4 | 0.0 |
| 48 Hours | 2.5 | 5/5 | 0 | 24.4 | 0.0 |
| 72 Hours | 5 | 5/5 | 0 | 24.4 | 0.0 |
| 72 Hours | 2.5 | 5/5 | 0 | 24.4 | 0.0 |
| 24 Hours | 5 | 5/5 | 0 | 14.6 | 0.0 |
| 24 Hours wash | | 5/5 | 0 | 11.0 | 0.0 |
| 24 Hours | 2.5 | 5/5 | 0 | 31.4 | 0.0 |
| 24 Hours wash | | 5/5 | 0 | 30.6 | 0.0 |
| 24 Hours | 1.25 | 5/5 | 0 | 31.4 | 0.0 |
| 24 Hours wash | | 5/5 | 0 | 30.6 | 0.0 |

TABLE 3
Dehydroabietylamine Acetate: Antipenetrant Effects of 50% Preparation vs. *S. mansoni* Cercariae in Mice

| Time | Conc. | Surv. | Mean Worm Burden Treated | Mean Worm Burden Control | % of Control |
|---|---|---|---|---|---|
| 24 Hours | 5 | 5/5 | 0 | 43.4 | 0.0 |
| 24 Hours | 2.5 | 4/4 | 0 | 43.4 | 0.0 |
| 48 Hours | 5 | 5/5 | 0 | 43.4 | 0.0 |
| 48 Hours | 2.5 | 5/5 | 0 | 43.4 | 0.0 |
| 48 Hours | 5 | 5/5 | 0 | 24.4 | 0.0 |
| 48 Hours | 2.5 | 5/5 | 0 | 24.4 | 0.0 |
| 72 Hours | 5 | 5/5 | 0 | 24.4 | 0.0 |
| 72 Hours | 2.5 | 5/5 | 0 | 24.4 | 0.0 |
| 24 Hours | 5 | 5/5 | 0 | 24.4 | 0.0 |
| 24 Hours wash | | 5/5 | 0 | 37.0 | 0.0 |
| 24 Hours | 2.5 | 5/5 | 0 | 24.4 | 0.0 |
| 24 Hours wash | | 5/5 | 1.2 | 37.0 | 3.2 |
| 48 Hours | 5 | 5/5 | 0 | 24.4 | 0.0 |
| 48 Hours wash | | 5/5 | 2.2 | 37.0 | 6.0 |
| 48 Hours | 2.5 | 5/5 | 0 | 24.4 | 0.0 |
| 48 Hours | | 5/5 | 1.8 | 37.0 | 4.9 |
| 24 Hours | 2.5 | 5/5 | 0 | 31.4 | 0.0 |
| 24 Hours wash | | 5/5 | 1.2 | 30.6 | 3.9 |
| 24 Hours | 1.25 | 5/5 | 0 | 31.4 | 0.0 |
| 24 Hours wash | | 5/5 | 0 | 30.6 | 0.0 |

TABLE 1-continued
Dehydroabietylamine: Antipenetrant Effects vs. *S. mansoni* Cercariae in Mice

| Time | Conc. | Surv. | Mean Worm Burden Treated | Mean Worm Burden Control | % of Control |
|---|---|---|---|---|---|
| 24 Hours wash | | 5/5 | 0 | 30.6 | 0.0 |

TABLE 4
Adduct of Dehydroabietylamine with Ethylene Oxide (1:5): Antipenetrant Effects vs. *S. mansoni* Cercariae in Mice

| Time | Conc. | Surv. | Mean Worm Burden Treated | Mean Worm Burden Control | % of Control | % of Suppression |
|---|---|---|---|---|---|---|
| 24 hr pre-treat. | 5% | 5/5 | 0 | 40.8 | 0 | 100% |
| 24 hr wash | 5% | 5/5 | 0.4 | 48.0 | 0.8 | 99.2 |
| 24 hr pre-treat. | 2.5% | 5/6 | 0.4 | 34.2 | 1.2 | 98.8 |
| 24 hr wash | 2.5% | 5/5 | 1.8 | 44.6 | 4.0 | 96.0 |
| 24 hr | 1.25% | 5/5 | 3.2 | 34.2 | 9.4 | 90.6 |

TABLE 4-continued

Adduct of Dehydroabietylamine with Ethylene
Oxide (1:5): Antipenetrant Effects vs.
S. mansoni Cercariae in Mice

| Time | Conc. | Surv. | Mean Worm Burden Treated | Mean Worm Burden Control | % of Control | % of Suppression |
|---|---|---|---|---|---|---|
| pre-treat. 24 hr wash | 1.25% | 4/4 | 30.8 | 44.6 | 69.1 | 30.9 |

TABLE 5

Adduct of Dehydroabietylamine with Ethylene
Oxide (1:11): Antipenetrant Effects vs.
S. mansoni Cercariae in Mice

| Time | Conc. | Surv. | Mean Worm Burden Treated | Con-trol | % of Control | % of Suppression |
|---|---|---|---|---|---|---|
| 24 hr | 5 | 5/5 | 0 | 33.2 | 0 | 100 |
| 24 hr | 2.5 | 5/5 | 0 | 33.2 | 0 | 100 |
| 48 hr | 5 | 5/5 | 15.6 | 33.2 | 47.0 | 53 |
| 48 hr | 2.5 | 5/5 | 14.4 | 33.2 | 43.4 | 56.6 |
| 24 hr | 2.5 | 5/5 | 0 | 40.8 | 0 | 100 |
| 24 hr wash | 2.5 | 5/5 | 31.8 | 48.0 | 66.2 | 33.8 |
| 24 hr | 5 | 5/5 | 5.0 | 28.4 | 17.6 | 82.4 |
| 24 hr wash | 5 | 5/5 | 38.6 | 52.2 | 74.0 | 26.0 |

I claim:

1. A method for preventing schistosomiasis in a mammal exposed to schistosome-infected water which comprises: applying to the skin of said mammal prior to exposure to the schistosome-infected water a composition comprising dehydroabietylamine or a pharmaceutically acceptable salt or adduct thereof in an amount sufficient to achieve an anti-penetrant effect against cercariae of infectious schistosome parasites.

2. A method according to claim 1 wherein the composition contains a compound selected from the group consisting of dehydroabietylamine, an ethylene oxide adduct thereof, and a pharmaceutically acceptable salt thereof.

3. A method according to claim 2 wherein the composition contains dehydroabietylamine.

4. A method according to claim 2 wherein the composition contains dehydroabietylamine acetate.

5. A method according to claim 2 wherein the composition contains an ethylene oxide adduct of dehydroabietylamine having 5 moles of ethylene oxide.

6. A method according to claim 2 wherein the composition contains an ethylene oxide adduct of dehydroabietylamine having 11 moles of ethylene oxide.

7. A method according to claim 2 for preventing infection by Schistosoma mansoni.

8. A method according to claim 2 for preventing infection by Schistosoma japonicum.

9. A method according to claim 2 for preventing infection by Schistosoma haematobium.

10. A method according to claim 2 wherein the composition is applied to the skin as a solution, a cream, an ointment, a liniment, or a malagma.

11. A method according to claim 10 wherein the solution is an alcoholic solution.

12. A method according to claim 1 wherein the concentration of compound in the composition is from about 1.25% w/v to about 5% w/v.

13. A method according to claim 2 wherein the concentration of compound in the composition is from about 1% to about 20% w/v.

14. A method according to claim 13 wherein the concentration of compound in the composition is from about 1% to about 10% w/v.

15. A method for preventing schistosomiasis in a mammal exposed to schistosome-infected water comprising applying to the skin of said mammal prior to exposure to the schistosome-infected water a composition consisting essentially of dehydroabietylamine or a pharmaceutically acceptable salt or adduct thereof in an amount sufficient to achieve an anti-penetrant effect against cercariae of infectious schistosome parasites.

16. A method according to claim 15 wherein the composition contains dehydroabietylamine ethylene oxide adduct.

* * * * *